United States Patent [19]

Gewald et al.

[11] Patent Number: 5,731,448

[45] Date of Patent: Mar. 24, 1998

[54] (+) AND (−)-8-CHLORO-6-SULFONYLOXY-OCTANOIC ACID, ITS DERIVATIVES, AND METHODS FOR MAKING

[75] Inventors: Rainer Gewald, Dresden; Gunter Laban, Langebrück; Thomas Beisswenger, Radebeul, all of Germany

[73] Assignee: Arzneimittelwerk Dresden GmbH, Germany

[21] Appl. No.: 705,212

[22] Filed: Aug. 29, 1996

[30] Foreign Application Priority Data

Aug. 19, 1996 [DE] Germany .................. 195 33 881.2

[51] Int. Cl.$^6$ .................. C07C 309/00; C07C 303/00; C07B 45/04
[52] U.S. Cl. .................. 554/85; 554/86; 554/88; 554/96
[58] Field of Search .................. 554/85, 86, 88, 554/96

[56] References Cited

PUBLICATIONS

Ohara et al., Chem. Abstr., vol. 78, abstr no. 147937 1973.

*Primary Examiner*—Gary Geist
*Assistant Examiner*—Deborah D. Carr
*Attorney, Agent, or Firm*—Schweitzer Cornman Gross & Bondell LL

[57] ABSTRACT

The synthesis of pure enantiomers of 8-chloro-6-sulfonyloxy-octanoic acids and their alkyl esters and of pure enantiomers of 6,8-dichloro-octanoic acid and its alkyl esters as intermediates for the synthesis of the enantiomers of α-liponic acid as well as a method for converting the two enantiomers of 8-chloro-6-hydroxy-octanoic acid into an enantiomer of α-liponic acid.

11 Claims, No Drawings

(+) AND (−)-8-CHLORO-6-SULFONYLOXY-OCTANOIC ACID, ITS DERIVATIVES, AND METHODS FOR MAKING

FIELD OF THE INVENTION

The present invention relates to (+) and (−)-8-chloro-6-sulfonyloxy-octanoic acid, enantiomers, and derivates, and methods for making.

BACKGROUND OF THE INVENTION

The R enantiomer of α-liponic acid is a natural product, which occurs in small concentrations in practically all animal and plant cells. α-Liponic acid is of vital importance as a coenzyme of the oxidative decarboxylation of α-ketocarboxylic acids (such as pyroracemic acid), is pharmacologically active and has antiphlogistic and antinociceptive (analgesic) as well as cyto-protective properties. An important pharmacological indication is the treatment of diabetic polyneuropathy. According to more recent results (such as in CA 116: 207360), α-liponic acid can be an important remedy for diseases caused by HIV-1 and HTLV IIIB viruses.

As disclosed, for example, in European patent No. 427,247 of Nov. 8, 1990, in the case of the pure optical isomers of α-liponic acid (R and S forms, that is, R-α-liponic acid and S-α-liponic acid), the R enantiomer, contrary to the racemate, has a predominantly antiphlogistic activity, and the S enantiomer has a predominantly antinociceptive (analgesic) activity. Therefore, the synthesis of the pure enantiomers, particularly of the R form, is of great importance.

Known methods for synthesizing enantiomerically pure α-liponic acid include splitting the racemate of α-liponic acid or its intermediates, asymmetric syntheses using chiral auxiliaries, "chiral pool" syntheses involving the use of naturally occurring, optically active starting compounds, as well as microbial syntheses (as described in survey articles: J. S. Yadav et al., J. Sci. Ind. Res. 1990, 49, 400; A. G. Tolstikov et al., Bioorg. Khim. 1990, 16, 1670; L. Dasaradhi et al., J. Chem. Soc., Chem. Commun. 1990, 729; A. S. Gopalan et al., J. Chem. Perking Trans. 1 1990, 1897; A. S Gopalan et al., Tetrahedron Letters 1989, 5705; and in European patent No. 487,986 of Nov. 14, 1991)

Of these, racemate splitting by forming diastereoisomeric salts of α-liponic acid with optically active α-methylbenzylamine, as described in German published patent application No. 44,137,773.7, of Nov. 16, 1991, represents the most economic method so far. However, the disadvantage of this method is that the separation of the racemate takes place only in the last step of the synthesis sequence and that the undesirable enantiomer of α-liponic acid can neither be racemized nor inverted. In other known methods of splitting the racemic intermediate of α-liponic acid, in each case only one enantiomer can be converted into the desired optical isomer of α-liponic acid. Accordingly, a theoretical yield of only 50% can be attained (see E. Walton et al., J. Am. Chem. Soc. 1955, 77, 5144; D. S. Acker and W. J. Wayne, J. Am. Chem. Soc. 1957, 79, 6483; and L. G. Chebotareva and A. M. Yurkevich, Khim.-Farm. Zh. 1980, 14, 92).

SUMMARY OF THE INVENTION

Accordingly, it is therefore an object of the invention to provide a method for the synthesis of enantiomerically pure α-liponic acids and dihydroliponic acids, for which the splitting of the racemate is carried out during the earliest possible step of the synthesis sequence, and the conversion of the two enantiomers of 8-chloro-6hydroxy-octanoic acid into an enantiomer of α-liponic acid with a theoretical yield of 100% being possible without additional racemization or inversion steps.

Accordingly, the present invention are (+)- and (−)-8-chloro-6-sulfonyloxy-octanoic acid enantiomers of formula (I), wherein $R^1$ is a linear and branched $C_{1-4}$ alkyl, or a $C_{6-8}$ aryl residue, and to their enantiomerically pure esters of formula (II). (Which is the same as formula (I) except that R is a $C_{1-4}$ alkyl residue).

The method of the invention is for the synthesis of enantiomerically pure α-liponic acids of formula (IV), as well as of enantiomerically pure dihydroliponic acids of formula (V) from the pure enantiomers of 8-chloro-6-hydroxy-octanoic acid of formula (VI). The present invention also relates to new esters of (+)- and (−)-6,8-dichloro-octanoic acids of formula (III), as well as to process for their synthesis and for synthesizing enantiomerically pure α-liponic acids of formula (IV) where R is a $C_{2-4}$ alkyl residue, as well as enantiomerically pure dihydroliponic acids of formula (V). α-Liponic acid is 1,2-dithiolane-3-pentanoic acid (thioctic acid).

The compound of formula (I) is prepared in accordance with the present invention by contacting a compound of formula (IV) with from about 1.5 to about 3 molar equivalents of sulfonyl chloride, and from about 1.5 to about 2.5 molar equivalents of tertiary nitrogen base at a temperature from about 0° C. to about 30° C. in an organic solvent.

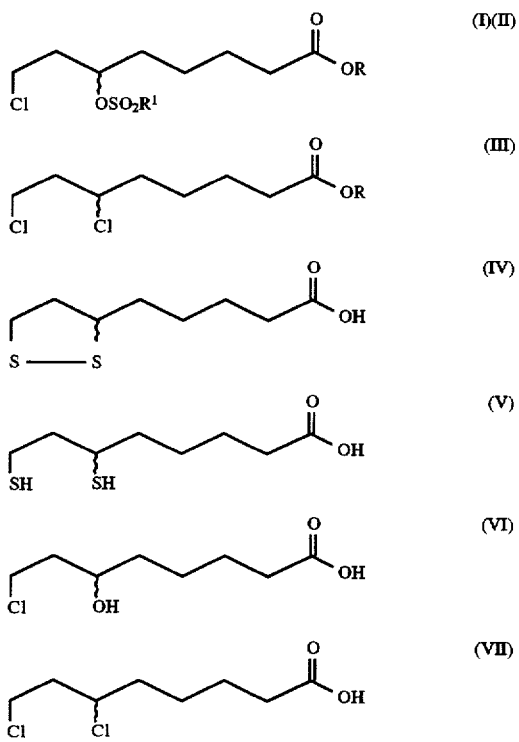

In the two slightly different reaction schemes that follow show the paths for respectively synthesizing R(+)- and S(−)-α-liponic acid wherein, R is suitably a linear or branched $C_{1-4}$ alkyl residue, that is, suitably a methyl, ethyl, n-propyl, iso-propyl, n-butyl, iso-butyl or t-butyl, most suitably a methyl residue, and R' is suitably a methyl or p-tolyl residue. $R^2$ is suitably a methyl or p-tolyl carboxylate of $R^1$, and $R^1$ is suitably a C-methyl e.g. $(CH_2)_4$—COOH, or a $C_{6-8}$ aryl e.g. $(CH_2)_4$—COOR) residue.

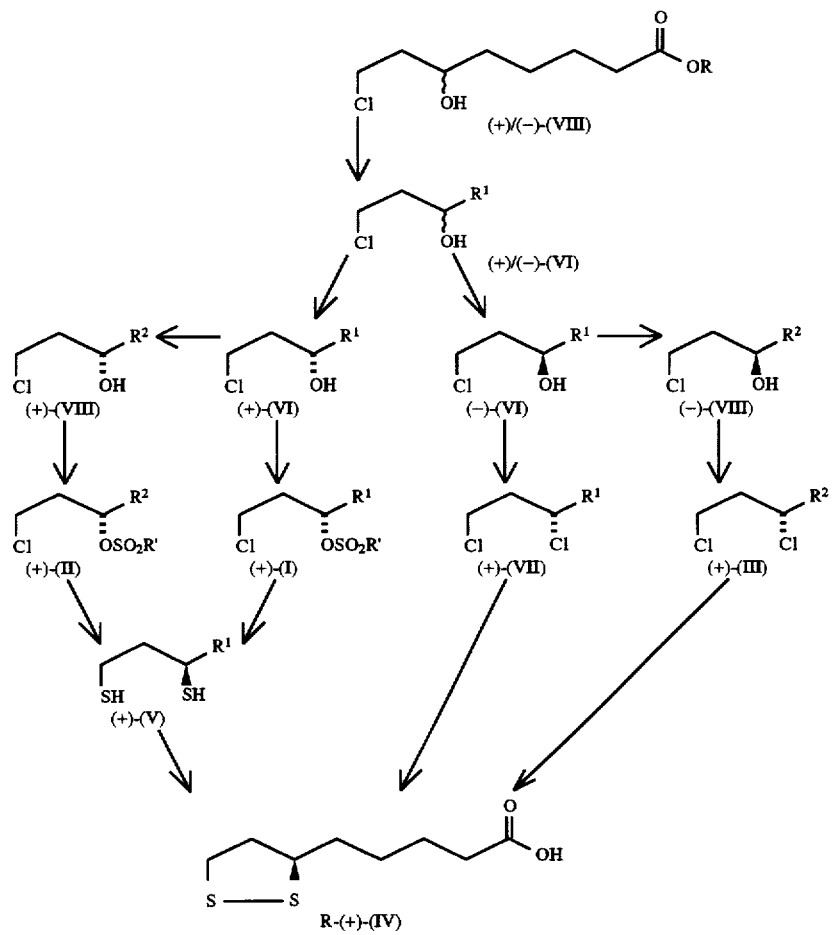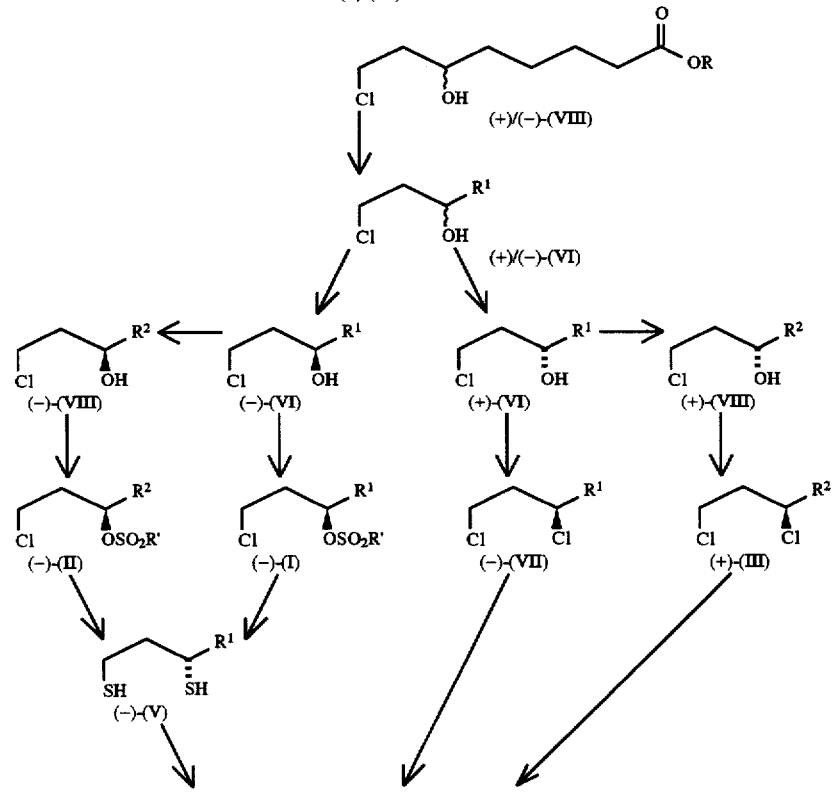

-continued

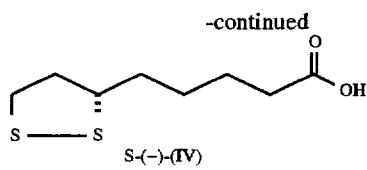
S-(−)-(IV)

DETAILED DESCRIPTION

The starting material of the method, the racemic 8-chloro-6-hydroxy-octanoic acid of formula (VI), is obtained by methods known per se by the hydrolysis of its racemic alkyl esters of formula (VIII), as described, for example, by Y. Deguchi and K. Nakanishi, in Yakugaku Zasshi 1963, 83 701.

The pure (+)-8-chloro-6-hydroxy-octanoic acid or the pure (−)-8-chloro-6-hydroxy-octanoic acid can be obtained by the reaction of the racemic 8-chloro-6-hydroxy-octanoic acid with the optical antipodes of α-methylbenzylamine, the formation of the diastereoisomeric salt pairs and the isolation of the less soluble salt, with subsequent splitting of the pure diastereoisomeric salts of (+)-8-chloro-6-hydroxy-octanoic acid and R-(+)-α-methylbenzylamine, or (−)-8-chloro-6-hydroxy-octanoic acid and S-(−)-α-methylbenzylamine with an addition of acid, such as a mineral acid, or base, such as alkali hydroxides.

Pursuant to the present invention, both enantiomers of 8-chloro-6-hydroxy-octanoic acid of formula (VI) can be converted directly into R-α-liponic acid of formula (+)-(IV) by reacting 8-chloro-6-hydroxy-octanoic acid or its alkyl esters with a sulfonyl chloride while retaining the configuration and chlorinating the (−)-8-chloro-6-hydroxy-octanoic acid or its alkyl esters with inversion of the configuration. The subsequent introduction of sulfur into any of the intermediates finally leads to R-α-liponic acid of excellent optical purity, with an enantiomeric excess (e.e)>99%, chiral HPLC).

The enantiomers of 8-chloro-6-hydroxy-octanoic acid of formula (VI) can be stereospecifically converted with retention of the configuration in the presence of catalytic amounts of HCl into their alkyl esters of formula (VIII), suitably into their methyl esters.

The enantiomerically pure alkyl esters of (+)-8-chloro-6-hydroxy-octanoic acid of formula (+)-(VIII) are then converted, with the retention of the configuration, into alkyl esters of (+)-8-chloro-6-sulfonyloxy-octanoic acid of formula (+)-(II), and these are converted into (−)-dihydroliponic acid of formula (−)-(I) or into R-α-liponic acid of formula (+)-(IV).

It is, however, also possible to start out from (+)-8-chloro-6-hydroxy-octanoic acid of formula (+)-(VI) and, over the (+)-8-chloro-6-sulfonyloxy-octanoic acid of formula (+)-(I), arrive in good yield and stereospecifically at (−)-dihydroliponic acid of formula (−)-(V) or R-α-liponic acid of formula (+)-(IV). The reaction with sulfonyl chloride is then carried out using from about 1.5 to about 3, and suitably from about 2.0 to about 2.2 molar equivalents of sulfonyl chloride, and from about 1.5 to about 2.5 and suitably, from about 2.0 to about 2.1 molar equivalents of a tertiary nitrogen base, suitably triethylamine.

The conversion of the enantiomerically pure dihydroliponic acid of formula (V) into the optical isomers of α-liponic acid of formula (IV) by oxidation with air in the presence of catalytical amounts of iron(III) salts is known from the literature, such as was described by E. Walton et al., in J. Am. Chem. Soc. 1955, 77 5144.

The enantiomerically pure alkyl esters of (−)-8-chloro-6-hydroxy-octanoic acid of formula (−)-(VIII) are converted with inversion of configuration by reaction with thionyl chloride in the presence of catalytic amounts of pyridine into the alkyl esters of (+)-6,8-dichloro-octanoic acid of formula (+)-(VII). The subsequent introduction of sulfur with $Na_2S_2$ yielded R-α-liponic acid of formula (+)-(IV) of high enantiomeric purity.

Advantageously, the alkyl esters of (−)-8-chloro-6-hydroxy-octanoic acid of formula (−)-(VI) are also converted directly in good yield into the (+)-6,8-dichloro-octanoic acid of formula (+)-(VII) in that from about 1.5 to about 5 and most suitably however from about 2.0 to about 2.5 molar equivalents of thionyl chloride are used in the chlorination step and the reaction mixture is worked up hydrolytically in a single reactor procedure by the addition of aqueous bases, preferably of sodium hydroxide. The further reaction of (+)-6,8-dichloro-octanoic acid with $Na_2S_2$ to R-α-liponic acid of formula (+)-(IV) is known from the literature such as from D. S. Acker and W. J. Wayne, J. Am. Chem. Soc. 1957, 79, 6483.

By reacting the (−)-8-chloro-6-hydroxy-octanoic acid of formula (−)-VI or its alkyl esters of formula (−)-(VIII) with sulfonyl chlorides and chlorinating the (+)-8-chloro-6-hydroxy-octanoic acid of formula (+)-(VI) or its alkyl esters of formula (+)-(VIII), S-α-liponic acid of formula S-(−)-(IV) can be obtained pursuant to the invention by a method similar to that described above.

For the synthesis of enantiomerically pure (+)- or (−)-dihydroliponic acid, S(−)-α-liponic acid, or R(+)-α-liponic acid can also be reduced a procedure known per se.

All the above-mentioned reactions are suitably carried out in a suitable organic solvent. Examples of organic solvents are $C_{3-10}$ aliphatic hydrocarbons aromatic hydrocarbons, which are liquids, esters of aliphatic or $C_{2-6}$ cycloaliphatic carboxylic acids, and $C_{2-6}$ aliphatic or cycloaliphatic alcohols, $C_{1-6}$ aliphatic or cycloaliphatic alcohols, ethers and glycol ethers or homogeneous mixtures of the aforementioned solvents. Ethyl acetate, cyclohexane, toluene, ethanol and their homogeneous mixtures are particularly suitable as solvents.

The purity of the optical isomers and of the diastereoisomeric salts was determined by means of the specific optical rotation. Furthermore, the relative contents of the optical isomers of 8-chloro-6-hydroxy-octanoic acid of formula (VI) and of the α-liponic acid of formula (IV) were determined by HPLC on optically active columns with a limit of detection of 0.5%. In addition, the optical purity of the alkyl esters of 8-chloro-6-hydroxy-octanoic acid of formula (VIII) was determined by the $^1$H-NMR analysis of the alkyl esters, which are formed by the reaction with (S)-(+)-O-acetylmandelic acid.

The present invention makes the enantiomers of α-liponic acid available in a simple and economical manner in high chemical and optical yield. The invention is illustrated in greater detail by the following examples.

EXAMPLE 1

Racemic 8-chloro-6-hydroxy-octanoic acid (+)/(−)-(VI) (39.9 g, 204 mmoles) was dissolved at 40° C. in 155 ml of a (1:1) mixture of ethyl acetate and cyclohexane. Over a period of 10 minutes, 13.5 g (112 mmoles) of R-(+)-α-methylbenzylamine were added. Subsequently, the mixture was cooled over a period of 2 hours to 20° C. and filtered and the precipitate was washed with 20 ml of the 1:1 ethyl acetate/cyclohexane solvent mixture and then with 30 ml of cyclohexane. The salt was recrystallized twice from 400 ml of 3:1 ethyl acetate/cyclohexane and dried under vacuum at 40° C. The (+)(+)-diastereoisomeric salt, α=+22.7° (c=1; ethanol) was obtained in a yield of 20.5 g.

The salt was suspended at 20° C. in 220 ml of diethyl ether and cooled in ice, after which the pH was slowly adjusted with 3N hydrochloric acid and stirring to a value of 1, the salt going into solution. After a further 30 minutes, the phases were separated and the organic phase washed once with 20 ml of 2N HCl and twice with 20 ml of water and dried over magnesium sulfate. After removal of the solvent under vacuum, 10.8 g (54% of the theoretical) of (+)-8-chloro-6-hydroxy-octanoic acid (+)-(VI) were obtained; $[\alpha]_D^{20}$=+24.5° (c=1; ethanol), e.e.>99% (HPLC), melting point 29°–30° C.

EXAMPLE 2

Racemic 8-chloro-6-hydroxy-octanoic acid (+)/(−)-(VI) (33.9 g, 173 mmoles) was dissolved at 40° C. in 130 ml of a (1:1) mixture of ethyl acetate and cyclohexane. Over a period of 10 minutes, 11.5 g (95 mmoles) of S-(−)-α-methylbenzylamine were added. Subsequently, the mixture was cooled over a period of 2 hours to 20° C. and filtered and the precipitate was washed with 17 ml of the 1:1 ethyl acetate/cyclohexane solvent mixture and subsequently with 25 ml of cyclohexane. The salt was recrystallized twice from 340 ml of 3:1 ethyl acetate/cyclohexane and dried under vacuum at 40° C. The (+)(+)-diastereoisomeric salt, α=−22.7° (c=1; ethanol) was obtained in a yield of 17.2 g.

The salt was suspended at 20° C. in 190 ml of diethyl ether and cooled in ice, after which the pH was slowly adjusted with 3N hydrochloric acid and stirring to a value of 1, the salt going into solution. After a further 30 minutes, the phases were separated and the organic phase washed once with 17 ml of 2N HCl and twice with 20 ml of water and dried over magnesium sulfate. After removal of the solvent under vacuum, 9.1 g (53% of the theoretical yield) of (−)-8-chloro-6-hydroxy-octanoic acid (−)-(VI) were obtained; $[\alpha]_D^{20}$=−24.5° (c=1; ethanol), e.e.>99% (HPLC), melting point 29°–30° C.

EXAMPLE 3

(+)-8-Chloro-6-hydroxy-octanoic acid (+)-(VI) (6.4 g, 32.9 mmoles) was refluxed for 2 hours in 100 ml of absolute methanol after the addition of 0.4 ml of concentrated hydrochloride. After that, the solvent was evaporated under vacuum. The methyl ester of (+)-8-chloro-6-hydroxy-octanoic acid (+)-(VIII), (R=Me) was obtained in a yield of 6.6 g (97% of the theoretical yield). $[\alpha]_D^{20}$=+24.5° (c=1, ethanol), e.e.:>99% ($^1$H-NMR).

EXAMPLE 4

(−)-8-Chloro-6-hydroxy-octanoic acid (−)-VI (7.7 g (39.5 mmoles) was refluxed for 2 hours in 120 ml of absolute methanol after the addition of 0.5 ml of concentrated hydrochloric acid. After that, the solvent was evaporated under vacuum. The methyl ester of (−)-8-chloro-6-hydroxy-octanoic acid (−)-(VIII) (R=Me) was obtained in a yield of 7.9 g (97% of the theoretical yield). $[\alpha]_D^{20}$=−24.5° (c=1, ethanol), e.e>99% ($^1$H-NMR).

EXAMPLE 5

(+)-8-Chloro-6-hydroxy-octanoic acid (+)-VI (3.9 g, 20 mmoles) and 4.1 g (40 mmoles) of triethylamine were mixed in 80 ml of toluene. While cooling to maintain an internal temperature of 10° to 15° C., 3.5 g (30.6 mmoles) of methanesulfonyl chloride were added slowly, stirring was continued for 30 minutes. After the addition of 25 ml of water, stirring was continued for a further 30 minutes, after which the organic phase was separated off and dried over magnesium sulfate. Subsequently, the solvent was removed under vacuum. (+)-8-Chloro-6-methanesulfonyloxy-octanoic acid (+)-(I) (R'=Me). $[\alpha]_D^{20}$=+32.9° (c=1; ethanol) was obtained in a yield of 3.8 g (69% of the theoretical yield).

EXAMPLE 6

(−)-8-Chloro-6-hydroxy-octanoic acid (+)-(VI) (6.6 g, 34 mmoles) and 7.0 g (68 mmoles) of triethylamine were mixed in 140 ml of toluene. While cooling to maintain an internal temperature of 10° to 15° C., 6.0 g (52.6 mmoles) of methanesulfonyl chloride were added slowly. Stirring was continued for 30 minutes. After the addition of 40 ml of water, stirring was continued for a further 30 minutes, after which the organic phase was separated off and dried over magnesium sulfate. Subsequently, the solvent was removed under vacuum. (+)-8-Chloro-6-methanesulfonyloxy-octanoic acid (+)-(I) (R'=Me). $[\alpha]_D^{20}$=+32.9° (c=1; ethanol) was obtained in a yield of 6.5 g (70% of the theoretical yield).

EXAMPLE 7

The methyl ester of (+)-8-chloro-6-hydroxy-octanoic acid (+)-(VIII) (R=Me) (4.0 g, 19.2 mmoles) and 1.97 g (19.2 mmoles) of triethylamine were mixed in 90 ml toluene. While cooling to an internal temperature of 10° to 15° C., 2.63 g (23.0 mmoles) of methanesulfonyl chloride were added slowly. Stirring was continued for 30 minutes. After the addition of 30 ml of water, stirring was continued for a further 30 minutes, after which the organic phase was removed and dried over magnesium sulfate. The solvent was then evaporated under vacuum. The methyl ester of (+)-8-chloro-6-methanesulfonyloxy-octanoic acid (+)-(II) (R=R'=Me) was obtained in a yield of 4.8 g (88% of the theoretical yield). $[\alpha]_D^{20}$=+31.2° (c=1; ethanol).

EXAMPLE 8

The methyl ester of (−)-8-chloro-6-hydroxy-octanoic acid (−)-(VIII), (R=Me) (2.1 g, 10 mmoles) and 1.0 g (10 mmoles) of triethylamine were mixed in 40 ml of toluene. While cooling to an internal temperature of 10° to 15° C., 1.4 g (12 mmoles) of methanesulfonyl chloride were added slowly. Stirring was continued for 30 minutes. After the addition of 25 ml of water, stirring was continued for a further 30 minutes, after which the organic phase was removed and dried over magnesium sulfate. The solvent was then evaporated under vacuum. The methyl ester of (−)-8-chloro-6-methanesulfonyloxy-octanoic acid (−)-(II), (R=R'=Me) was obtained in a yield of 2.5 g (88% of the theoretical yield). $[\alpha]_D^{20}$=−31.3 (c=1; ethanol).

EXAMPLE 9

To a solution of 2.4 g (11.0 mmoles) of the methyl ester of (+)-8-chloro-6hydroxy-octanoic acid (+)-(VIII) (R=Me) and 0.04 g (0.5 mmoles) of pyridine in 8 ml toluene, 1.6 g (13.5 mmoles) of thionyl chloride in 5 ml of toluene were added slowly. The mixture was then refluxed for 1 hour. After cooling to room temperature, the reaction mixture was added to 20 ml ice water and the organic phase was separated and washed with 10 mL of water and dried over magnesium sulfate. After that, the solvent was evaporated under vacuum. The methyl ester of (−)-6,8-Dichloro-octanoic acid (−)-(III), (R=Me) was obtained in a yield of 2.0 g (81% of the theoretical yield). $[\alpha]_D^{20}$=−30.0° (c=1, benzene).

EXAMPLE 10

To a solution of 2.9 g (13.2 mmoles) of the methyl ester of (−)-8-chloro-6-hydroxy-octanoic acid (−)-(VIII), (R=Me) and 0.05 g (0.6 mmoles) of pyridine in 10 ml toluene, 1.9 g (16.2 mmoles) of thionyl chloride in 6 ml toluene were added slowly. The mixture was then refluxed for 1 hour. After cooling to room temperature, the reaction mixture was added to 25 ml ice water and the organic phase was separated and washed with 10 mL of water and dried over magnesium sulfate. After that, the solvent was evaporated under vacuum. The methyl ester of (+)-6,8-dichloro-octanoic acid (+)-(III), (R=Me) was obtained in a yield of 2.4 g (81% of the theoretical yield). $[\alpha]_D^{20}$=+30.1° (c=1, benzene).

EXAMPLE 11

To a solution of 2.4 g (12.3 mmoles) of (+)-8-chloro-6-hydroxy-octanoic acid (+)-(VI) and 0.05 g (0.6 mmoles) of pyridine in 30 ml toluene, 3.3 g (27.7 mmoles) of thionyl chloride were added slowly. The mixture was then refluxed for 1 hour. The reaction mixture was cooled to room temperature and added to 50 ml ice water. The organic phase was then removed, washed with 20 ml water and stirred for 4 hours with 30 ml of 2N NaOH. The aqueous phase was then removed, adjusted to a pH of 1 with 3N HCl and extracted twice with 20 ml diethylether. The combined ether extracts were dried over magnesium sulfate. After that, the solvent was evaporated under vacuum. (−)-6,8-dichloro-octanoic acid (−)-(VII) was obtained in a yield of 2.1 g (80% of the theoretical yield). $[\alpha]_D^{20}$=−30.6° (c=1; benzene).

EXAMPLE 12

To a solution of 3.0 g (15.4 mmoles) of (−)-8-chloro-6-hydroxy-octanoic acid (−)-(VI) and 0.06 g (0.8 mmoles) of pyridine in 40 ml toluene, 4.1 g (34.4 mmoles) of thionyl chloride were added slowly. The mixture was then refluxed for 1 hour, cooled to room temperature and added to 60 ml of ice water. The organic phase was then removed, washed with 20 ml of water and stirred for 4 hours with 35 ml of 2N NaOH. The aqueous phase was then removed, adjusted to a pH of 1 with 3N HCl and extracted twice with 20 ml of diethylether. The combined ether extracts were dried over magnesium sulfate. After that, the solvent was evaporated under vacuum. (+)-6,8Dichloro-octanoic acid (+)-(VII) was obtained in a yield of 2.6 g (80% of the theoretical yield). $[\alpha]_D^{20}$=+30.5° (c=1; benzene).

EXAMPLE 13

A mixture of 4.6 g (19 mmoles) of sodium sulfide nonahydrate and 0.61 g (19 mmoles) of sulfur in 40 ml ethanol was refluxed for 15 minutes. To this mixture, a solution of 4.9 g (17 mmoles) of the methyl ester of (+)-8-chloro-6-methanesulfonyloxy-octanoic acid (+)-(II), (R=R'=Me) in 5 ml ethanol was added at 20° C. over a period of 2 hours, after which stirring was continued for 3 hours, whereupon 24 ml of 10% sodium hydroxide were added and stirred for 2 hours at 25° C. After removal of the ethanol under vacuum at 25° C., a solution of 0.37 g (9.7 mmoles) of sodium borohydride in 10 mL of 1% sodium hydroxide was added over a period of 10 minutes to the reaction mixture, which was then stirred and heated slowly to 100° C. and stirred at this temperature for 1 hour. The reaction mixture was cooled, acidified to a pH of 1 with concentrated HCl and extracted twice with 20 ml diethyl ether. The organic phases were dried over sodium sulfate and the solvent evaporated under vacuum. (−)-Dihydroliponic acid (−)-(V) was obtained in a yield of 2.8 g (79% of the theoretical yield). $[\alpha]_D^{20}$=−13.7° (c=1.5; ethanol).

EXAMPLE 14

A mixture of 3.1 g (13 mmoles) of sodium sulfide nonahydrate and 0.41 g (13 mmoles) of sulfur in 25 ml ethanol was refluxed for 15 minutes. To this mixture, a solution of 3.3 g (11 mmoles) of the methyl ester of (−)-8-chloro-6-methanesulfonyloxy-octanoic acid (−)-(II) (R=R'=Me) in 5 ml ethanol was added at 20° C. over a period of 2 hours, after which stirring was continued for 3 hours, whereupon 15 ml of 10% sodium hydroxide were added and stirred for 2 hours at 25° C. After removal of the ethanol under vacuum at 25° C., a solution of 0.25 g (6.6 mmoles) of sodium borohydride in 10 ml of 1% sodium hydroxide was added over a period of 10 minutes to the reaction mixture, which was then stirred and heated slowly to 100° C. and stirred at this temperature for 1 hour. The reaction mixture was cooled, acidified to a pH of 1 with concentrated HCl and extracted twice with 15 ml of diethyl ether. The organic phases were dried over sodium sulfate and the solvent evaporated under vacuum. (+)-Dihydroliponic acid (+)-(V) was obtained in a yield of 1.9 g (83% of the theoretical yield). $[\alpha]_D^{20}$=+13.7° (c=1.5; ethanol).

EXAMPLE 15

A mixture of 1.5 g (6.3 mmoles) of sodium sulfide nonahydrate and 0.2 g (6.3 mmoles) of sulfur in 15 ml of ethanol was refluxed for 15 minutes. To this mixture, a solution of 1.5 g (5.5 mmoles) of (+)-8-chloro-6-methanesulfonyloxy-octanoic acid (+)-I in 4 ml of ethanol was added at 20° C. over a period of 2 hours, after which stirring was continued for 3 hours, whereupon 15 ml of 10% sodium hydroxide were added and stirred for 2 hours at 25° C. After removal of the ethanol under vacuum at 25° C., a solution of 0.12 g (3.2 mmoles) of sodium borohydride in 4 ml of 1% sodium hydroxide was added over a period of 10 minutes to the reaction mixture, which was then stirred and heated slowly to 100° C. and stirred at this temperature for 1 hour. The reaction mixture was cooled, acidified to a pH of 1 with concentrated HCl and extracted twice with 10 ml of diethyl ether. The organic phases were dried over sodium sulfate and the solvent evaporated under vacuum. (−)-Dihydroliponic acid (−)-(V) was obtained in a yield of 0.8 g (70% of the theoretical yield). $[\alpha]_D^{20}$=−13.5° (c=1.0; ethanol).

EXAMPLE 16

A mixture of 1.8 g (7.6 mmoles) of sodium sulfide nonahydrate and 0.24 g (7.6 mmoles) of sulfur in 18 ml of ethanol was refluxed for 15 minutes. To this mixture, a solution of 1.8 g (6.6 mmoles) of (−)-8-chloro-6-methanesulfonyloxy-octanoic acid (−)-I in 5 ml of ethanol was added at 20° C. over a period of 2 hours, after which stirring was continued for 3 hours, whereupon 18 ml of 10% sodium hydroxide were added and stirred for 2 hours at 25° C. After removal of the ethanol under vacuum at 25° C., a solution of 0.14 g (3.8 mmoles) of sodium borohydride in 5 ml of 1% sodium hydroxide was added over a period of 10 minutes to the reaction mixture, which was then stirred and heated slowly to 100° C. and stirred at this temperature for 1 hour. The reaction mixture was cooled, acidified to a pH of 1 with concentrated HCl and extracted twice with 10 ml of diethyl ether. The organic phases were dried over sodium sulfate and the solvent evaporated under vacuum. (+)-Dihydroliponic acid (+)-(V) was obtained in a yield of 1.0 g (73% of the theoretical yield). $[\alpha]_D^{20}=-13.6°$ (c=1.0; ethanol).

EXAMPLE 17

A mixture of 0.62 g (2.6 mmoles) of sodium sulfide nonahydrate and 0.08 g (2.6 mmoles) of sulfur in 10 ml ethanol was refluxed for 15 minutes. To this mixture, refluxing slightly, a solution of 0.55 g (2.4 mmoles) of the methyl ester of (+)-6,8-dichloro-octanoic acid (+)-(III) (R=Me) in 5 ml ethanol was added over a period of 1 hour, after which stirring was continued for 15 minutes and 8 ml of ethanol were distilled off, whereupon 10 ml of 0.5N NaOH were added and stirred for 12 hours at 25° C. After the reaction mixture was acidified to a pH of 1 with concentrated HCl, it was extracted twice with 20 ml diethyl ether, the organic phases were dried over sodium sulfate and the solvent evaporated under vacuum. By recrystallizing from cyclohexane, 0.28 g (57% of the theoretical yield) of R-(+)-α-liponic acid (+)-(IV) was obtained. Melting point 44° to 46° C., e.e.>99% (HPLC).

EXAMPLE 18

A mixture of 0.87 g (3.6 mmoles) of sodium sulfide nonahydrate and 0.11 g (3.6 mmoles) of sulfur in 15 ml ethanol was refluxed for 15 minutes. To this mixture, refluxing slightly, a solution of 0.77 g (3.4 mmoles) of the methyl ester of (−)-6,8-dichloro-octanoic acid (−)-(III) (R =Me) in 7 ml ethanol was added over a period of 1 hour, after which stirring was continued for 15 minutes and 12 ml of ethanol were distilled off, whereupon 14 ml of 0.5N NaOH were added and stirred for 12 hours at 25° C. After the reaction mixture was acidified to a pH of 1 with concentrated HCl, it was extracted twice with 20 ml diethyl ether, the organic phases were dried over sodium sulfate and the solvent evaporated under vacuum. By recrystallizing from cyclohexane, 0.38 g (54% of the theoretical yield) of S-(−)-α-liponic acid (−)-(IV) was obtained. Melting point 44° C. to 46° C., e.e.>99% (HPLC).

We claim:

1. (+)- or (−)-8-chloro-6-sulfonyloxy-octanoic acid enantiomers of the formula

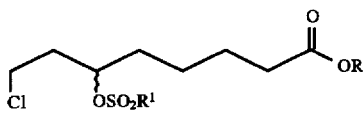

(I)

wherein R' is a linear and branched $C_{1-4}$ alkyl, or a $C_{6-8}$ aryl residue, and R is a hydrogen.

2. An alkyl ester of a (+)- and (−)-8-chloro-6-sulfonyloxy-octanoic acid enantiomer of the formula,

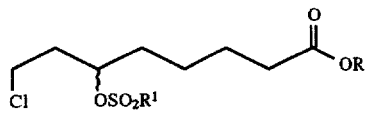

(II)

wherein R is a linear and branched $C_{1-4}$ alkyl residue and $R^1$ is a linear or branched $C_{1-4}$ alkyl residue, or a $C_{6-8}$ aryl residue.

3. An alkyl ester of (+)- or (−)-6,8-dichloro-octanoic acid enantiomers of the formula

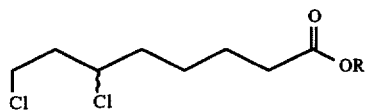

(III)

wherein R is a linear and branched $C_{1-4}$ alkyl residue.

4. A method for the synthesis of a (+)- or (−)-8-chloro-6-sulfonyloxy-octanoic acid of formula (I), which comprises contacting a respective (+)- or (−)-8-chloro-6-hydroxy-octanoic acid of the formula

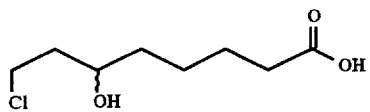

(VI)

with from about 1.5 to about 3 molar equivalents of sulfonyl chloride and from about 1.5 to about 2.5 molar equivalents of a tertiary nitrogen base at from about 0° C. to about 30° C. in an organic solvent.

5. A method for the synthesis of alkyl esters of (+)- or (−)-8-chloro-6-sulfonyloxy-octanoic acids of formula (II), which comprises contacting a respective alkyl ester of (+)- or (−)-8-chloro-6-hydroxy-octanoic acids of the formula

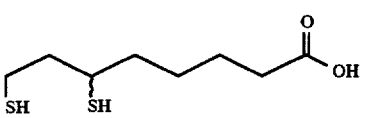

(VIII)

wherein R is a linear and branched $C_{1-4}$ alkyl residue, with from about 1.0 to about 1.5 molar equivalents of sulfonyl chloride, and from about 1.0 to about 1.5 molar equivalents of a tertiary nitrogen base at from about 0° C. to about 30° C. in an organic solvent.

6. A method for the synthesis of alkyl an ester of (+)- or (−)-6,8-dichloro-octanoic acid of the formula

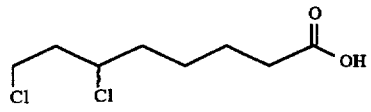

(VII)

which comprises contacting a respective alkyl ester of (+)- or (−)-8-chloro-6-hydroxy-octanoic acid of the formula

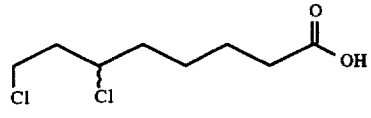

(VII)

with from about 1.0 to about 2.0 molar equivalents of thionyl chloride in the presence of catalytic amounts of pyridine at from about 60° C. to about 130° C. in an organic solvent.

7. A method for the synthesis of a (+)- or (−)-6,8-dichloro-octanoic acid of formula (VII), which comprises contacting a respective (+)- or (−)-8-chloro-6-hydroxy-octanoic acid of the formula (VI) with from about 1.5 to about 5.0 molar equivalents of thionyl chloride in the presence of a catalytic amount of pyridine at from about 60° to about 130° C. in an organic solvent.

8. A method for the synthesis of R-(+)-α-liponic acid of the formula

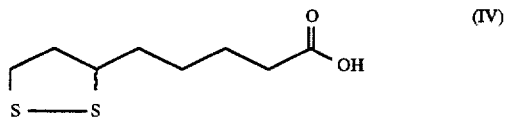

which comprises producing from (+)-8-chloro-6-hydroxy-octanoic acid of formula (+)-(VI), sulfonyl chloride, and a tertiary nitrogen base, (+)-8-chloro-6-sulfonyloxy-octanoic acid of formula (+)-(I) and converting the resulting product of formula (VI) with alkali metal disulfide/sulfur or thiourea to R-(+)-α-liponic acid (+)- of formula (IV), or (−)-dihydroliponic acid (−)- of the formula,

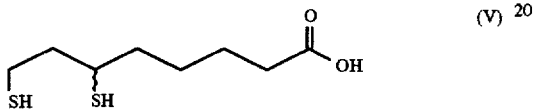

then oxidizing the compound of formula (V) to form a (+) compound of formula (IV), and producing a (+) 6,8-dichlorooctanoic acid of formula (+)(VII) by contacting a (−)-8-chloro-6-hydroxy-octanoic acid of formula (−)-(VI) with thionyl chloride, in the presence of pyridine, and converting the compound of formula (−) (VII) with alkali metal disulfide/sulfur into the compound of formula (+)-(IV).

9. A method for the synthesis of R-(+)-α-liponic acid of formula R-(+)-(IV), which comprises a) esterifying (+)-8-chloro-6-hydroxy-octanoic acid of formula (+)-VI to a compound of formula (+)-(VIII), and reacting the esterified product with a sulfonyl chloride and a tertiary nitrogen base to form an alkyl ester of (+)-8-chloro-6-sulfonyloxy-octanoic acid of formula (+)-(II), reacting the obtained alkyl ester with alkali metal disulfide/sulfur or thiourea to form R-(+)-α-liponic acid of formula (+)-(IV), or (−)-dihydroliponic acid of formula (−)-(V), and converting the last product by oxidation into the compound of formula (+)-(IV) and b) esterifying (−)-8-chloro-6-hydroxy-octanoic acid of formula (−)-(VI) to form a compound of formula (−)-(VIII), and reacting the so formed compound with thionyl chloride, in the presence of pyridine, to form an alkyl ester of (+)-6,8-dichloro-octanoic acid of formula (+)-(VII), and converting said alkyl ester with alkali metal disulfide/sulfur into the compound of formula (+)-(IV).

10. A method for the synthesis of S-(−)-α-liponic acid of formula (−)-(IV), which comprises a) synthesizing (−)-8-chloro-6-mesyloxy-octanoic acid of formula (−)-(I) from (−)-8-chloro-6-hydroxy-octanoic acid of formula (−)-(VI), with sulfonyl chloride and a tertiary nitrogen base, and reacting the product with alkali metal disulfide/sulfur or thiourea to form S-(−)-α-liponic acid of formula (−)-(IV), or (+)-dihydroliponic acid of formula (+)-(V), and converting the last said product by oxidation into the compound of formula (−)-(IV) and b) synthesizing (−)-6,8-dichloro-octanoic acid of formula (−)-(VII) from (+)-8chloro-6-hydroxy-octanoic acid of formula (+)-(VI) and thionyl chloride, in the presence of pyridine, and converting the product with alkali metal.

11. A method for the synthesis of S-(−)-α-liponic acid of formula (−)-(IV), which comprises a) esterifying (−)-8-chloro-6-hydroxy-octanoic acid of formula (−)-(VI) to form a compound of formula (−)-(VIII), converting the product with sulfonyl chloride and a tertiary nitrogen base into an alkyl ester of (−)-8-chloro-6-sulfonyloxy-octanoic acid of formula (−)-(II), reacting the last said product with an alkali metal disulfide/sulfur or thiourea to form S-(−)-α-liponic acid of formula (−)-(IV), or (+)-dihydroliponic acid of formula (+)-(V), and converting the last said products by oxidation into the compound of formula (−)-(IV), and b) esterifying (+)-8-chloro-6-hydroxy-octanoic acid of formula (+)-(VI) to a compound of formula (+)-(VIII), and synthesizing the alkyl ester of (−)-6,8-dichloro-octanoic acid of formula (−)-(VII) with thionyl chloride in the presence of pyridine, and converting the resulting product with alkali metal disulfide/sulfur into the compound of formula (−)-(IV).

* * * * *